(12) United States Patent
Kim et al.

(10) Patent No.: US 9,115,057 B2
(45) Date of Patent: Aug. 25, 2015

(54) CONJUGATE OF ARM-TYPE POLYETHYLENEGLYCOL WITH LINEAR POLYETHYLENEIMINE AS GENE CARRIER AND SYNTHESIS THEREOF

(75) Inventors: Won Jong Kim, Gyungbuk (KR); Ran Namgung, Gyeonggi-do (KR)

(73) Assignee: Postech Academy-Industry Foundation, Gyungbuk (KR)

( * ) Notice: Subject to any disclaimer, the term of this patent is extended or adjusted under 35 U.S.C. 154(b) by 776 days.

(21) Appl. No.: 13/122,667

(22) PCT Filed: Oct. 1, 2009

(86) PCT No.: PCT/KR2009/005643
§ 371 (c)(1),
(2), (4) Date: Apr. 28, 2011

(87) PCT Pub. No.: WO2010/041847
PCT Pub. Date: Apr. 15, 2010

(65) Prior Publication Data
US 2011/0311817 A1   Dec. 22, 2011

(30) Foreign Application Priority Data
Oct. 6, 2008 (KR) .................. 10-2008-0097741

(51) Int. Cl.
*C07C 233/36* (2006.01)
(52) U.S. Cl.
CPC ......... *C07C 233/36* (2013.01); *Y10T 428/2982* (2015.01)
(58) Field of Classification Search
CPC .................................................. C07C 233/36
USPC .................................. 525/435, 54.2; 428/402
See application file for complete search history.

(56) References Cited

U.S. PATENT DOCUMENTS

| 2001/0005717 A1* | 6/2001 | Wagner et al. ................... 514/44 |
| 2004/0096507 A1* | 5/2004 | Kwang et al. ................. 424/486 |
| 2008/0039547 A1 | 2/2008 | Khatri et al. |

FOREIGN PATENT DOCUMENTS

| EP | 1938795 | 7/2008 |
| WO | 2009/102952 | 8/2009 |

OTHER PUBLICATIONS

Petersen et al., "Star-Shaped Poly(ethylene glycol)-block-polyethylenimine Copolymers Enhance DNA Condensation of Low Molecular Weight Polyethylenimines," Biomacromolecules, 3, 926-936, 2002.*
Kleemann, et al. Nano-carriers for DNA delivery to the lung based upon a TAT-derived peptide covanlently coupled to PEG-PEI, Journal of Controlled Release, 109, 299-316, 2005.*
Lungwitz, U. et al., Polyethyleimine-based non-viral gene delivery systems, European Journal of Pharmaceutics and Biopharmaceutics, 2005, 60, pp. 247-266.
Lee, H. et al., A new gene delivery formulation of polyethylenimine/DNA complexes coated with PEG conjugated fusogenic peptide, Journal of Controlled Release, 2001, 76, pp. 183-192.

(Continued)

*Primary Examiner* — Paul A Zucker
*Assistant Examiner* — Mark Luderer
(74) *Attorney, Agent, or Firm* — Thompson Hine LLP

(57) ABSTRACT

Disclosed are a gene carrier in which polyethyleneglycol is conjugated with polyethyleneimine and a method for the synthesis thereof. The gene carrier is useful in transferring DNA, siRNA and negatively charged peptides.

20 Claims, 9 Drawing Sheets

(56) References Cited

OTHER PUBLICATIONS

Kursa, M. et al., Novel Shielded Transferrin-Polyethylene Glycol-Polyethylenimine/DNA Complexes for Systemic Tumor-Targeted Gene Transfer, Bioconjugate Chem. 2003, 14, pp. 222-231.

Erbacher, P. et al., Transfection and Physical Properties of Various Saccharide, Poly(ethylene glycol), and Antibody-Derivatized polyethylenimines (PEI), The Journal of Gene Medicine, 1999, 1, pp. 210-222.

Ogris, M. et al., Tumor-targeted gene therapy: strategies for the preparation of ligand-polyethylene glycol-polyethylenimine/DNA complexes, Journal of Controlled Release, 2003, 91, 173-181.

Kichler, A. et al., Intranasal gene delivery with a polyethylenimine-PEG conjugate, Journal of Controlled Release, 2002, 81, pp. 379-388.

Supplementary European Search Report, EP 09819354, Oct. 17, 2014, 3 pages.

\* cited by examiner

CONJUGATE OF ARM-TYPE POLYETHYLENEGLYCOL WITH LINEAR POLYETHYLENEIMINE AS GENE CARRIER AND SYNTHESIS THEREOF

TECHNICAL FIELD

The present invention relates to a gene carrier. More particularly, the present invention relates to a gene carrier composed of polyethylene glycol and polyethyleneimine and a method for the synthesis thereof.

BACKGROUND ART

Gene therapy is very attractive because its ability to cure conventionally incurable diseases on the genetic level. For gene therapy, a gene responsible for curing a disease must be carried by a carrier, which are typically classified into viral and non-viral vectors.

In spite of low delivery efficiency, non-viral vectors have been extensively studied because of the safety thereof.

Of the non-viral vectors, polyethyleneimine (PEI) is recognized to have highly efficient gene delivery and serve as an effective gene carrier in vitro and in vivo (O. Boussif, F. Lezoualc'h, M. A. Zanta, M. D. Mergny, D. Scherman, B. Demeneix, J. P. Behr, A versatile vector for gene and oligonucleotide transfer into cells in culture and in vivo: polyethylenimine. Proc. Natl. Acad. Sci. USA 92 (1995) 7297-7301; and W. T. Godbey, K. K. Wu, A. G. Mikos, Poly(ethylenimine) and its role in gene delivery, J. controlled Release 60 (1999) 149-160).

Korean Pat. Unexamined Publication No. 2006-25711 discloses a gene carrier composed mainly of a copolymer of polyethyleneimine and polyether as a substitute for PEI 25K which although high in gene transfer efficiency is of limited use in practical application due to the high cytotoxicity thereof.

However, there is still a need for gene carriers which are more efficient and of lower cytotoxicity.

DISCLOSURE OF INVENTION

Technical Problem

It is therefore an object of the present invention to provide a novel gene carrier which has advantages over conventional gene carriers in terms of gene transfer efficiency and cytotoxicity.

It is another object of the present invention to provide a method for the synthesis of the novel gene carrier which is advantageous over conventional carriers in terms of gene transfer efficiency and cytotoxicity.

It is a further object of the present invention to provide a gene transfer method by which a gene of interest can be effectively transferred with high safety.

It is still a further object of the present invention to provide a gene-polymer complex which can transfect at high efficiency and is stable to the external environment.

Solution to Problem

In order to accomplish the above objects, there is provided a compound, represented by Chemical Formula 1:

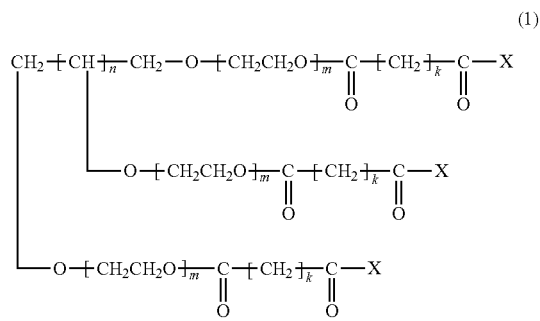

wherein, n is an integer from 1 to 4, m is different or the same integers representing repeat units, k is an integer from 1 to 8, and X is —NH-A for at least one arm with proviso —OH is assigned to the remainder of the arms wherein A represents —CH$_2$CH$_2$—(NHCH$_2$CH$_2$)$_z$—NHCH$_2$CH$_2$NH$_2$ and Z is an integer, or a salt or ester thereof.

Also, provided is a compound, represented by Chemical Formula 3:

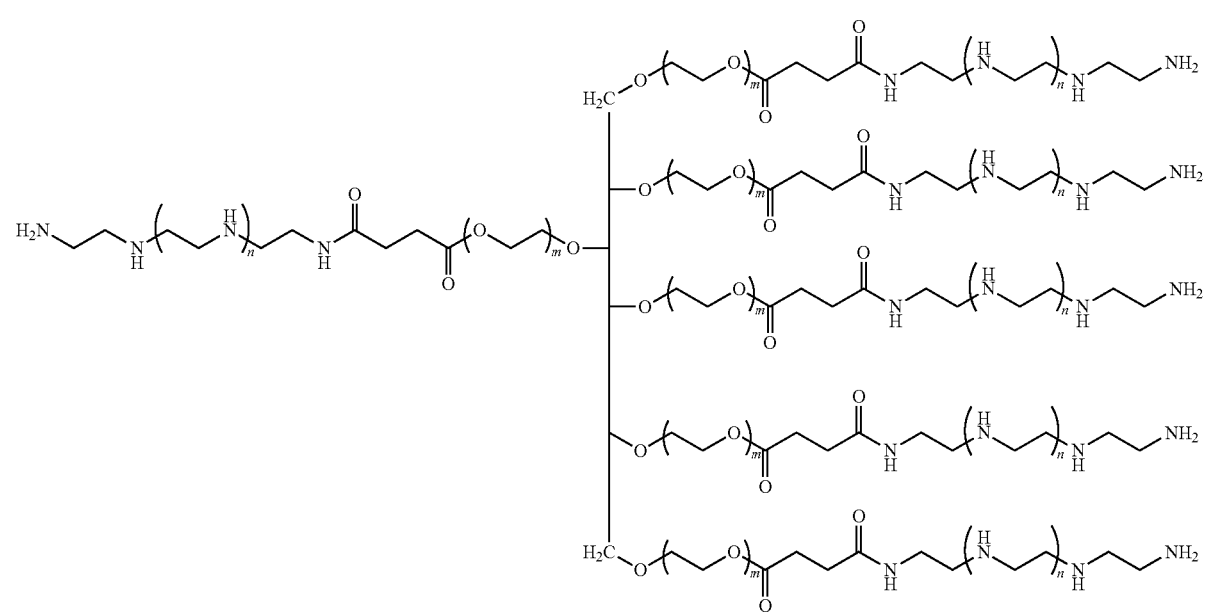

wherein, m and n are independently integers representing repeat units, or a salt or ester thereof.

Also, provided is a compound, represented by Chemical Formula 4:

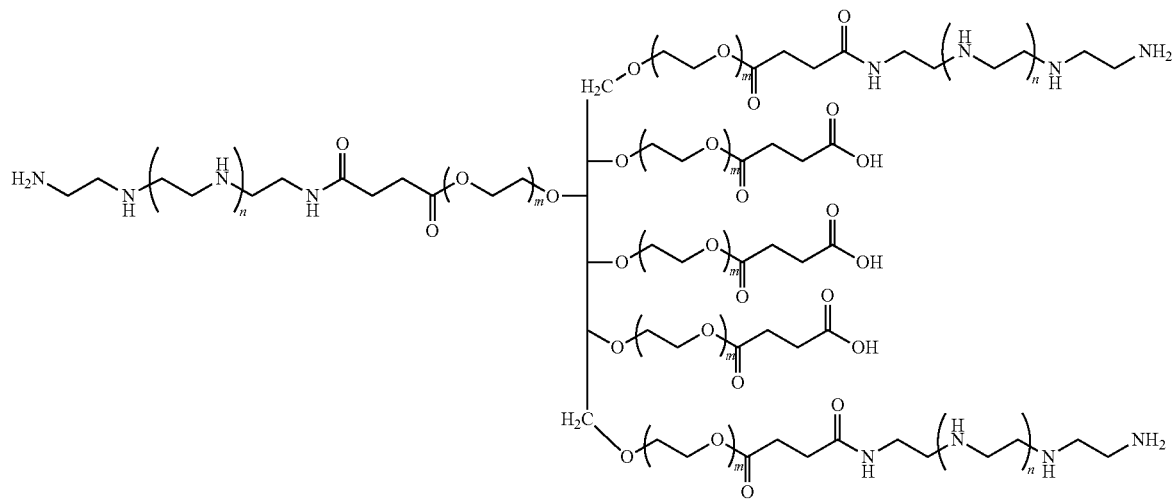

(4)

wherein m and n are independently integers representing repeat units.

In another aspect, there is provided a method of synthesizing a gene carrier, comprising reacting an arm-type polyethyleneglycol, represented by Chemical Formula 5:

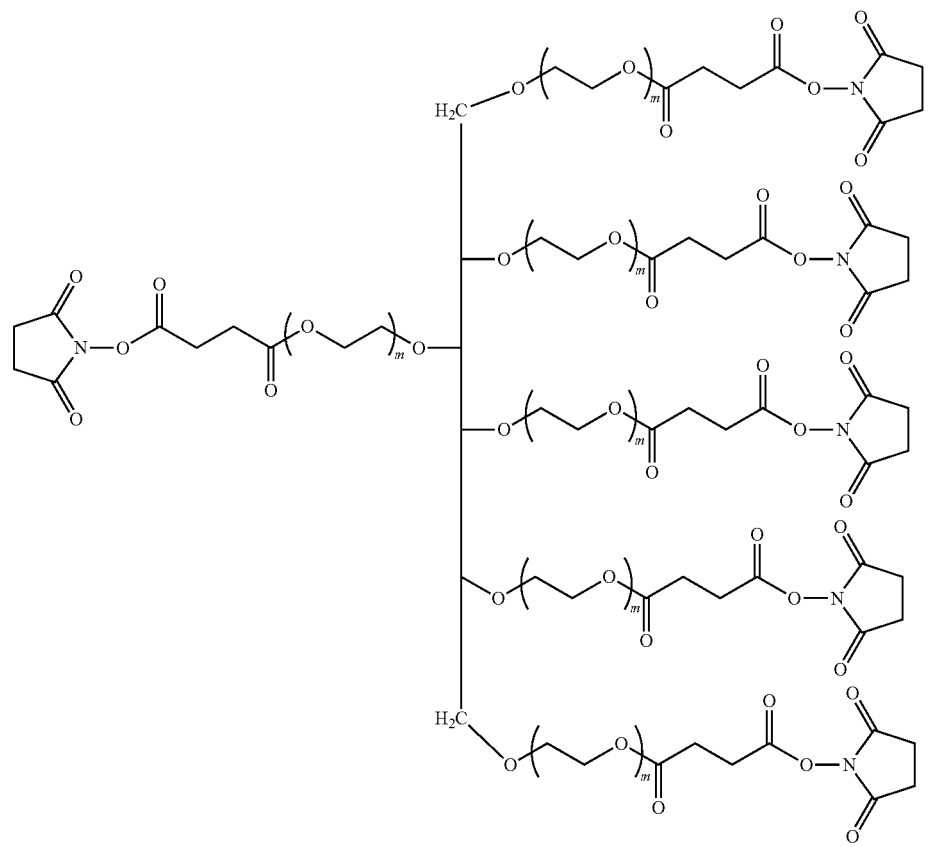

(5)

wherein, m is integers which are representing repeat units, with a polyethyleneimine represented by Chemical Formula 6:

$$H_2N-CH_2CH_2-(NHCH_2CH_2)_z-NHCH_2CH_2NH_2 \quad (6)$$

wherein, z is an integer.

In a further aspect, there is provided a polymer-gene complex, comprising: a compound composed of arm-type polyethyleneglycol conjugated with linear polyethyleneimine, represented by Chemical Formula 1:

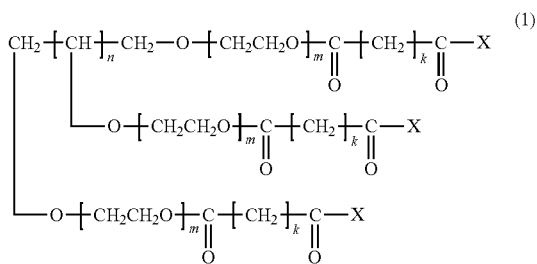

wherein,
n is an integer from 1 to 4,
m is different or the same integers representing repeat units,
k is an integer from 1 to 8, and
X is —NH-A for at least one arm with proviso —OH is assigned to the remainder wherein A represents —$CH_2CH_2$—($NHCH_2CH_2$)—$NHCH_2CH_2NH_2$ and Z is an integer, or a salt or ester thereof; and a gene.

In still a further aspect, there is provided a method for transferring a gene, comprising: reacting a three- to six-arm type polyethylene with polyethyleneimine to afford a conjugated compound; and associating the conjugated compound with a gene.

As described above, the present invention provides a gene carrier composed of a polyethyleneglycol moiety and a polyethyleneimine moiety and a method for the synthesis thereof. The gene carrier of the present invention encompasses a gene of interest therein during transfer, so that it protects the gene from the external environment. Also, the gene carrier shows low cytotoxicity thanks to a low molecular weight of the polyethyleneimine moiety as well as having a good gene transfer efficiency.

In addition, the polymer-gene complex formed by associating the gene carrier with a gene is on the order of approximately 200 nm in size, which is suitable for penetration into cells.

BEST MODE FOR CARRYING OUT THE INVENTION

Figure 1:
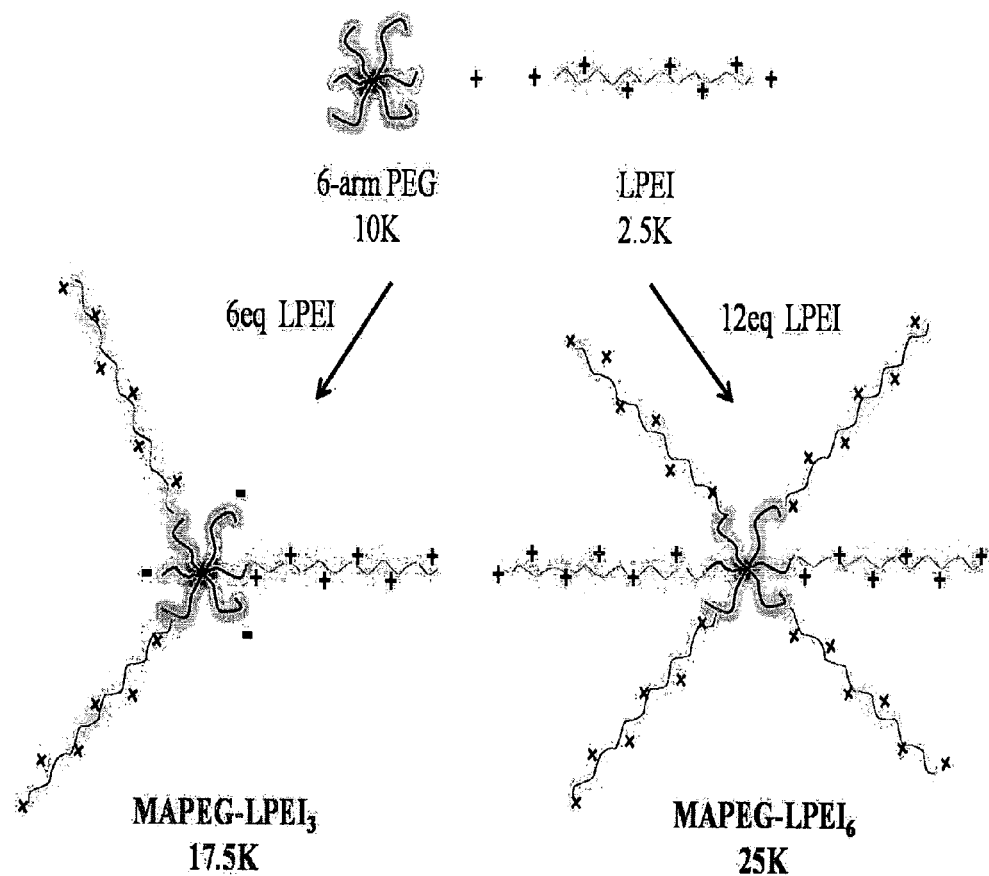
FIG. 1 is a schematic view showing the synthesis of MAPEG-LPEI.

In accordance with an aspect thereof, the present invention provides a compound, represented by the following Chemical Formula 1, in which an arm-type polyethylene glycol is conjugated with a linear polyethyleneimine, or a salt or ester derivative thereof.

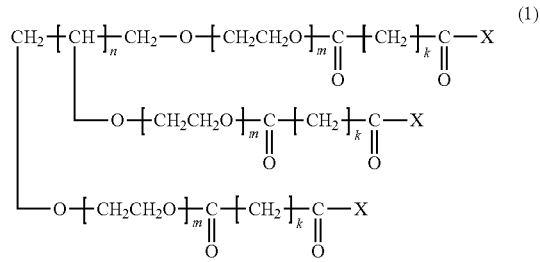

wherein,
n is an integer from 1 to 4,
m is a repeating unit of the same or different integers,
k is an integer of from 1 to 8, and
X is —NH-A for at least one arm with the assignment of —OH to the remainder wherein A represents —$CH_2CH_2$—($NHCH_2CH_2$)$_Z$—$NHCH_2CH_2NH_2$ and Z is an integer.

In the present invention, freedom is given to the size of the polyethylene glycol arms upon the synthesis thereof, so that suitable sizes of polyethyleneglycol can be reacted with linear polyethyleneimine.

In accordance with another aspect thereof, the present invention provides as a gene carrier a conjugate of 6-arm polyethyleneglycol and liner polyethyleneimine, represented by the Chemical Formula 2, or its salt or ester derivative:

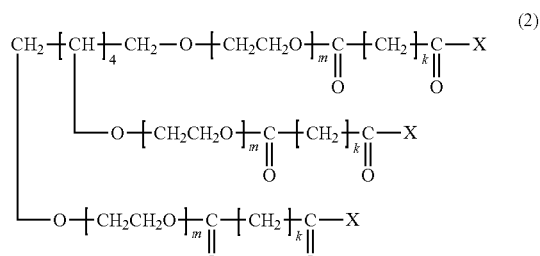

wherein, m is a repeating unit of the same or different integers for each arm, k is 2, X is —NH-A for at least one arm with the assignment of —OH to for the remaining arms wherein A represents —CH$_2$CH$_2$—(NHCH$_2$CH$_2$)$_Z$—NHCH$_2$CH$_2$NH$_2$ and Z is an integer.

In a preferred modification, the gene carrier of the present invention is a compound in which all of the six arms of polyethyleneglycol are conjugated with polyethyleneimine, as represented by Chemical Formula 3:

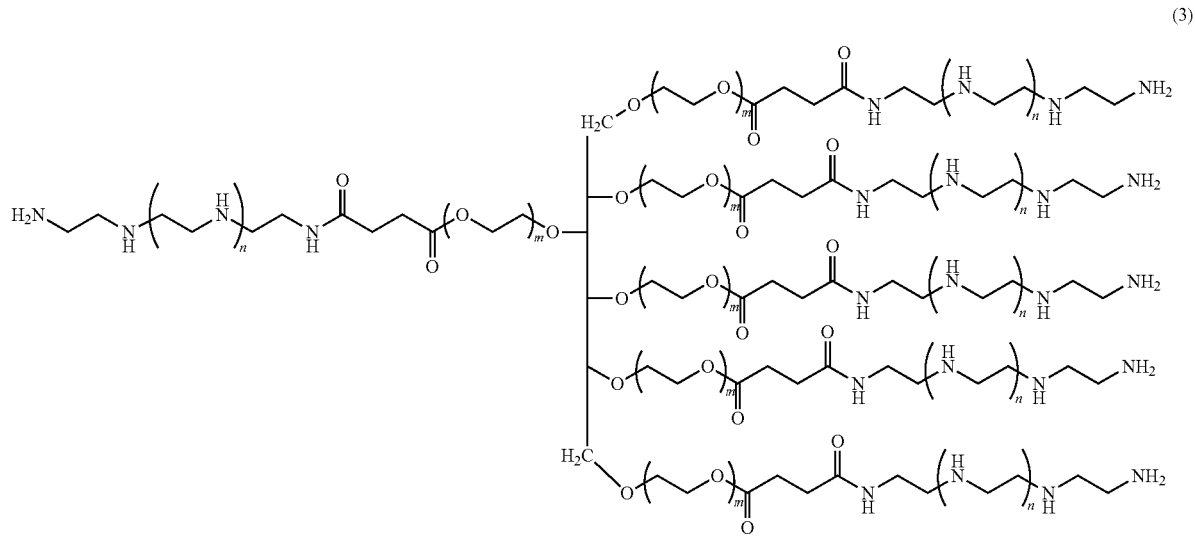

(3)

wherein, m and n are independently repeating units of the same or different integers for each arm, or a salt or ester derivative thereof.

In another preferred embodiment, the gene carrier of the present invention is a compound in which three of the six arms of polyethyleneglycol are conjugated with polyethyleneimine while —COOH is attached to the other three, as represented by Chemical Formula 4:

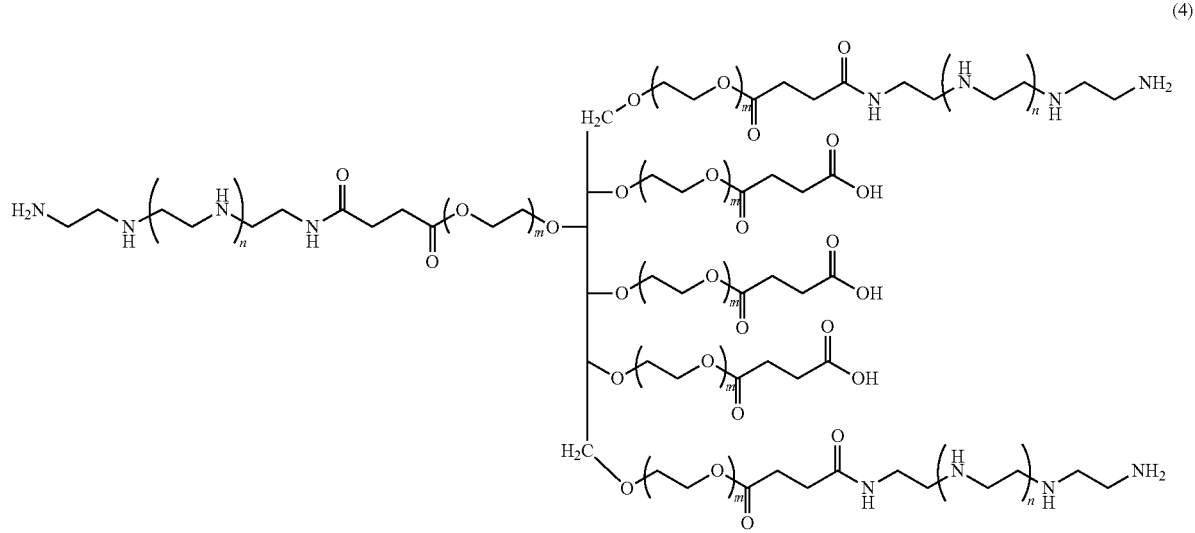

(4)

wherein, m and n are independently repeating units of different or the same integers for each arm, or a salt or ester derivative thereof.

In accordance with another aspect thereof, the present invention provides a method for the synthesis of a gene carrier represented by the following Chemical Formula 1:

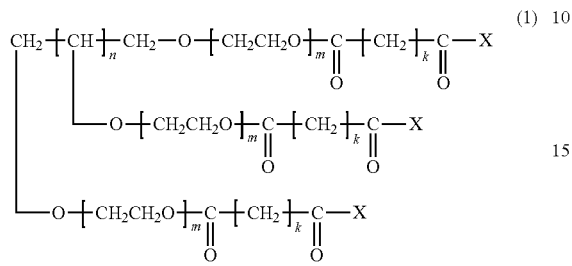

wherein, n is an integer from 1 to 4, m is a repeating unit of the same or different integers, k is an integer from 1 to 8, and X is —NH-A for at least one arm with the assignment of —OH to the remainder wherein A represents —CH$_2$CH$_2$—(NHCH$_2$CH$_2$)$_z$—NHCH$_2$CH$_2$NH$_2$ and Z is an integer, by reacting an arm-type polyethyleneglycol, represented by the following Chemical Formula 5:

wherein m is as defined above, with a polyethyleneimine represented by the Chemical Formula 6:

$$H_2N-CH_2CH_2-(NHCH_2CH_2)_z\text{-}NHCH_2CH_2NH_2 \qquad (6)$$

wherein, z is an integer.

In an embodiment of the present invention, when the linear polyethyleneimine (LPEI) is reacted with arm-type polyethyleneglycol (PEG), the ester groups of the arms which remain unreacted are hydrolyzed into —COOH ends. The reaction may be carried out in a buffer containing an acid such as HCl.

In a preferred embodiment, the arm-type polyethyleneglycol and linear polyethyleneimine range in molecular weight from 5 to 20 k and from 1 to 10 k, respectively. More preferably, the arm-type polyethyleneglycol and the linear polyethyleneimine are about 10 k and 2.5 k in molecular weight, respectively. When too small an arm-type polyethyleneglycol is used, the gene carrier has poor water solubility. On the other hand, too large an arm-type polyethyleneglycol may cause a decrease in gene transfer efficiency. As per the linear polyethyleneimine, if its molecular weight is smaller than the lower limit the gene transfer efficiency of the gene carrier may be poor while it may show cytotoxicity as its molecular weight is over the upper limit.

In accordance with a further aspect thereof, the present invention provides a polymer-gene complex in which a conjugate of arm-type polyethyleneglycol and linear polyethyleneimine, represented by the following Chemical Formula (1):

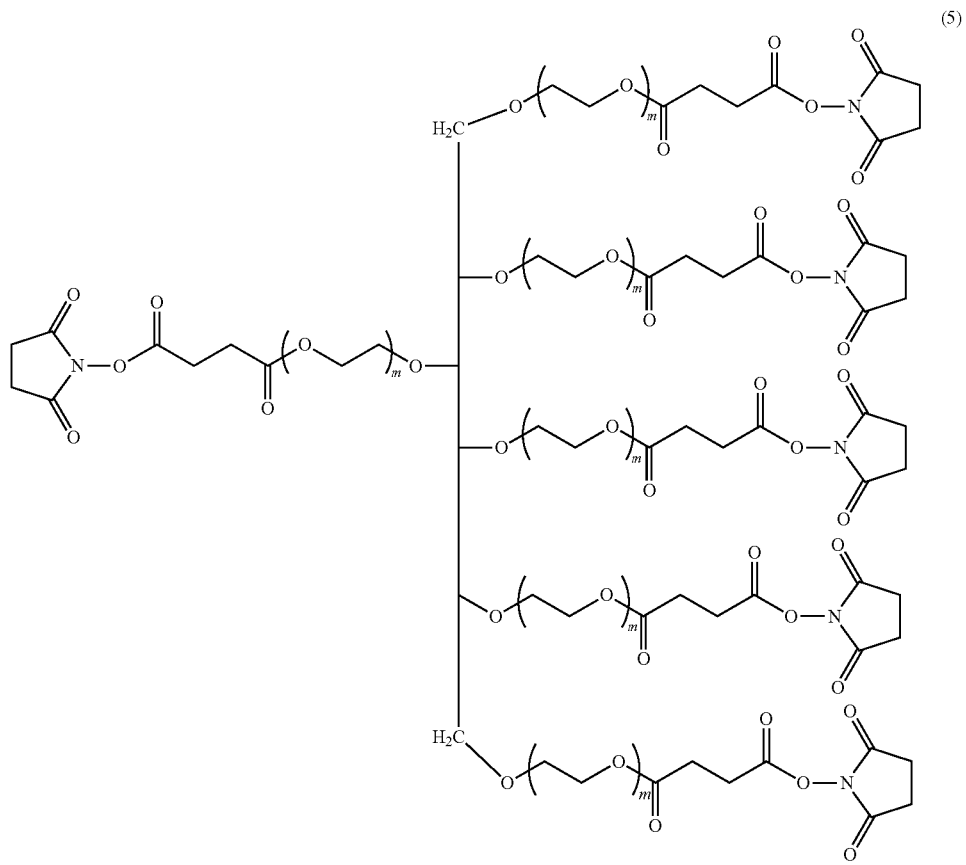

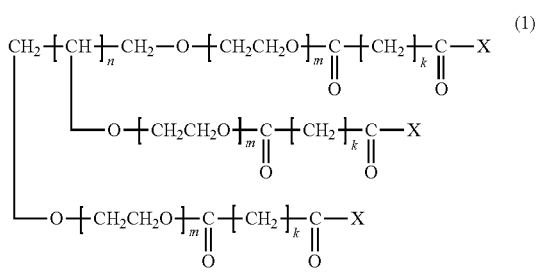

wherein,
n is an integer from 1 to 4,
m is a repeating unit of the same or different integers,
k is an integer from 1 to 8, and
X is —NH-A for at least one arm with the assignment of —OH to the remainder wherein A represents —CH$_2$CH$_2$—(NHCH$_2$CH$_2$)$_z$—NHCH$_2$CH$_2$NH$_2$ and Z is an integer, or a salt or ester derivative thereof, is associated with a gene.

Although theoretically established, the gene carrier of the present invention is adapted to protect a gene of interest from the external environment when associated therewith. Examples of the gene to be transferred by the carrier of the present invention include DNA, RNA, e.g., siRNA, and oligonucleotides.

Together with a gene, the gene carrier forms a complex which is small enough to penetrate into cells. The complex is typically on the order of hundreds in size, preferably 300 nm or less in size, and more preferably 200 nm or less in size.

The linear polyethyleneimine preferably has such a low molecular weight of from 1 to 10 K as to show low cytotoxicity, and more preferably a molecular weight of approximately 2.5 K.

In accordance with still a further aspect thereof, the present invention provides a method for transferring a gene, comprising:
reacting 3- to 6-arm polyethyleneglycol with polyethyleneimine to give a conjugate; and
associating the conjugate with a gene to form a polymer-gene complex.

Polyethyleneglycol can be synthesized into various sizes of differing molecular weights if necessary and so long as it conjugates with polyethyleneimine at the arm ends thereof, any polyethyleneglycol may be used without limitation in the present invention.

At the end of each arm of polyethyleneglycol is a functional group which can conjugate with polyethyleneimine.

Examples of the functional group through which the arm-type polyethyleneglycol can be conjugated to linear polyethyleneimine include N-hydroxysuccinimide ester, nitrophenyl, isocynate, sulfonyl chloride, aldehyde, glyoxal, epoxide, carbonate, cyanuric halide, dithiocarbonate, tosylate, and maleimide with preference for N-hydroxysuccinimide capable of forming an amide bond.

In an embodiment of the present invention, the polyethyleneglycol is designed to have a number of arms sufficient for encompassing the gene to be complexed therewith. Preferably, the polyethyleneglycol is of a six-arm type, with each arm conjugating with polyethyleneimine.

The complex formed when the conjugate is associated with a gene is water soluble. Because of higher cytotoxicity of its larger molecular weight, polyethyleneimine is low in molecular weight, for example, 2.5 K.

MODE FOR THE INVENTION

A better understanding of the present invention may be obtained through the following examples which are set forth to illustrate, but are not to be construed as limiting the present invention.

1. Materials

6-Arm polyethyleneglycol succinimidyl succinate can be synthesized as follows or is commercially available from, for example, SunBio Corp. Korea. Linear polyethyleneimine (LPEI) was purchased from PolyScience Inc. (Warrington, Pa., U.S.A.).

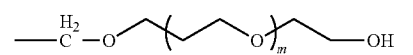

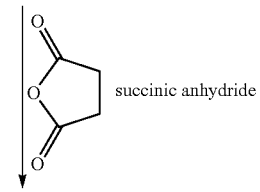
succinic anhydride

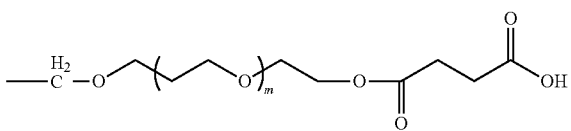

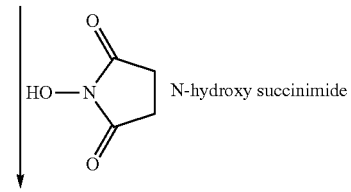
N-hydroxy succinimide

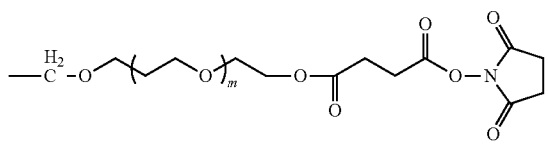

2. MAPEG-LPEIx Synthesis

LPEI was conjugated with 6-arm PEG through a bond between an amino group and an ester group. For this, 0.18 mmol or 0.36 mmol of LPEI was reacted with 0.03 mol of h-arm PEG.

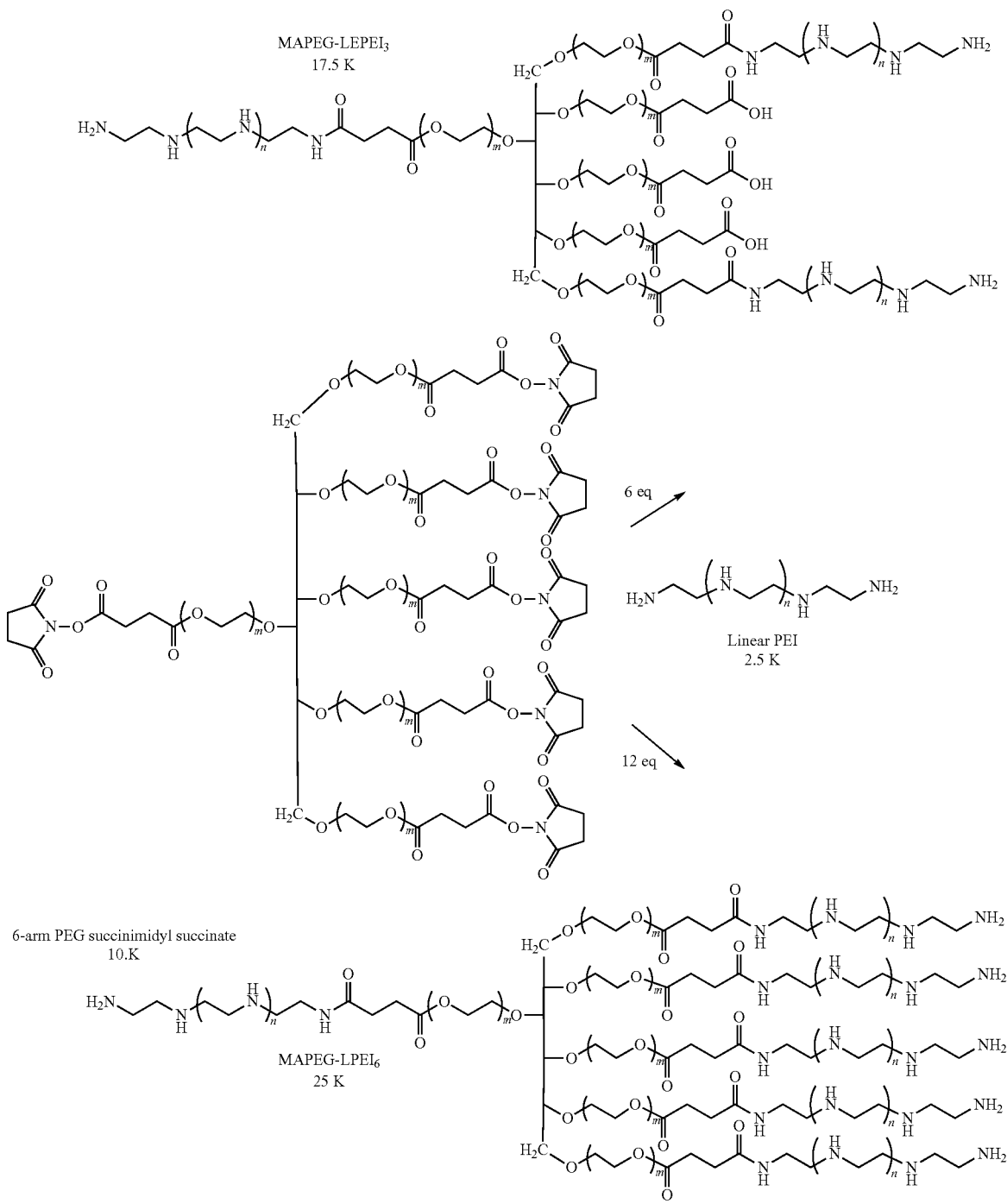

First, 6-arm PEG (300 mg, 0.03 mmol) was dissolved in 1.5 ml of PBS buffer. LPEI (0.18 or 0.36 mmol) was dissolved in 5 ml of PBS in the presence of 2M HCl. This LPEI in PBS was added to PEG in PBS, followed by incubation at room temperature for 24 hrs. The reaction mixture was dialyzed against distilled water for 1 day (dialysis tubing with MWCO 3500 Da). The reaction product was collected and freeze dried.

The molar ratio of LPEI to PEG in the product was calculated from $^1$H-NMR using Bruker DPX 300 MHZ Spectroscopy. As for specimens for this spectroscopy, they were prepared by dissolving the products in deuterium oxide ($D_2O$).

Relative molecular weights were measured using size exclusion chromatography (SEC, Shimadzu, Kyoto, Japan) equipped with a refractive index detector (RID-10A, Shimadzu, Kyoto, Japan) and a column (TSK gel GMPW, Tosoh Co. Ltd., Japan) while deionized water was used as a mobile phase moving at a flow rate of 1 ml/min at room temperature.

3. Gel Retardation Assay.

Polymer/p DNA complexes (polyplexes) were prepared at various N/P ratios from 0.5 to 100 in PBS buffer, followed by incubation at room temperature for 30 min. The polyplexes were run on 1% (w/v) agarose gel containing ethidium bromide (0.5 μg/mL) therein in TAE (Tris-acetate-EDTA) buffer for 20 min in the presence of 100 V.

4. Particle Size and Zeta Potential Measurements.

A polymer solutions was added at an N/P ratio to a pDNA solution to afford a polyplex the concentration of which was then adjusted into 33 μg/mL, followed by incubation for 30 min at room temperature. The polyplex was measured for particle size and zeta potential using Dynamic Light Scattering.

5. Stability of pDNA in Serum

A MAPEG-LPEI/pDNA complex (w/w ratio=5) or free pDNA (10 μg) was incubated at 37° C. in a PBS solution containing 30% FBS. After incubation for 0, 1, 3, 6, 12 and 24 hrs, 10 μl of each of the samples was transferred into an Eppendorf tube and stored at −80° C. until use. Each sample was thawed and mixed with 2 μl of 10% sodium dodecyl sulfate (SDS) before electrophoresis for 20 min in an electric field of 100 V.

6. Luciferase Reporter Gene Expression

Hela cells were seeded at a density of $4 \times 10^4$ cells/well onto 24-well plates containing DMEM 500 μl of DMEM supplemented with 10% FBS per well which were then incubated for 24 hrs at 37° C. in a humidified 5% $CO_2$ atmosphere. For the formation of polyplexes, 1 μg of pDNA in 10 μl of PBS buffer was added at predetermined w/w ratios to 10 μl of a polymer in PBS, followed by incubation for 30 min at room temperature. Cells were incubated with the polyplexes for 4 hours in 250 μl of serum-free DMEM and for a further 20 hours in 500 μl of DMEM supplemented with 10% FBS. The cells were washed twice with 500 μl of PBS and dialyzed with 200 μl of lysis buffer per well. Luciferase gene expression was measured with a microplate spectrofluorometer (VICTOR 3 V Multilabel Counter, Perkin Elmer Wellesley, Mass., U.S.A.).

7. Cell Viability Assay

Hela cells were seeded at a density of $1 \times 10^4$ cells/well onto 96-well plates before incubation for 24 hours. pDNA (0.2 μg/μl) was complexed at a predetermined w/w ratio with a polymer in PBS buffer and incubated for 30 min before use. The polyplexes were incubated with the cells for 4 hours in 100 μl of a serum-free medium and then for a further 20 hours in 200 μl of DMEM supplemented with 10% FBS. An MTT solution (20 μl, 5 mg/mL) was added, followed by the incubation of the cells for an additional 4 hours. After removal of the medium, 150 μl of DMSO was added to each well to dissolve internalised purple formazan crystals. 100 μl of each sample was taken and transferred into new 96-well plates.

Absorbance at 570 nm was read in a microplate spectrofluorometer and expressed as percentages of the control that has not been exposed to the transfection system.

Result Analysis

Data are described with reference to the accompanying drawings.

1. Synthesis of MAPEG-LPEIs

Figure 2:
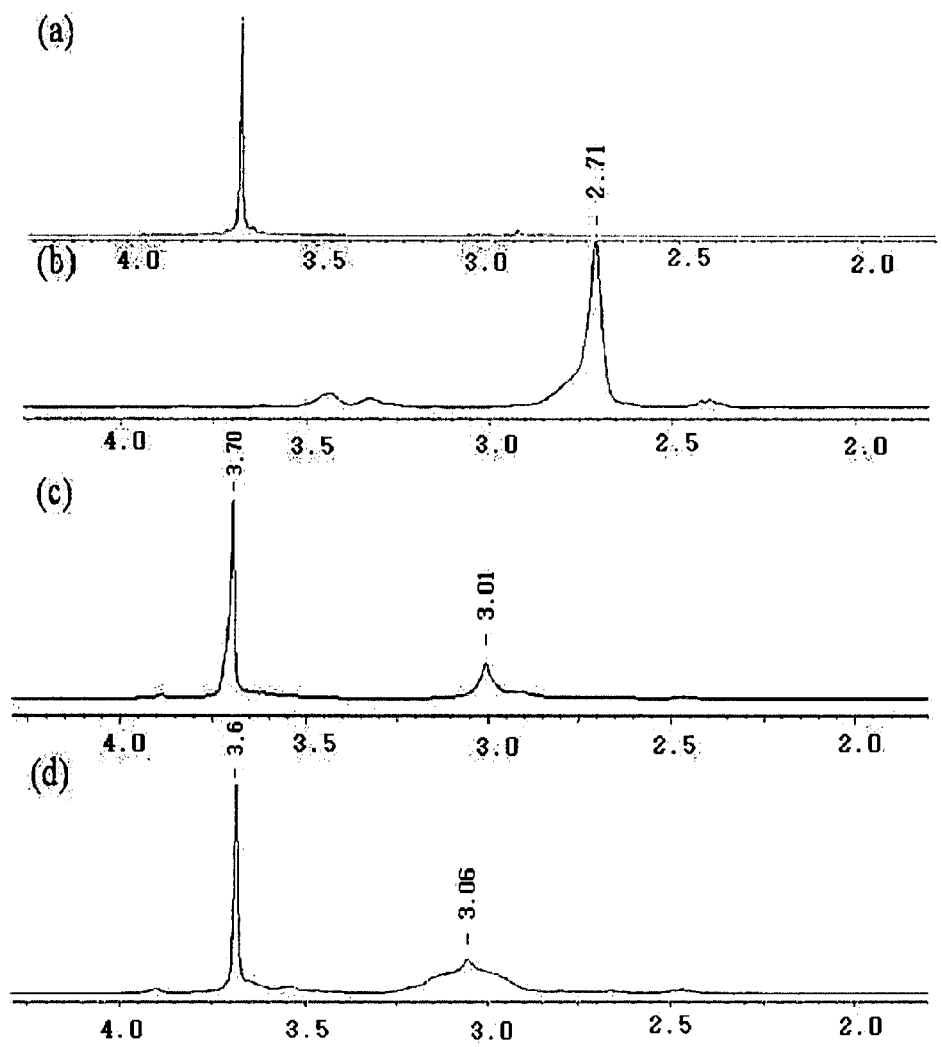
FIG. 2 is $^1$H-NMR spectra of compounds with peaks at 3.70 ppm (c) and 3.01 ppm (d) resulting from conjugation between 6-arm PEG with a peak at 3.69 ppm (a) and LPEI with a peak at 2.71 ppm (b).

MAPEG-LPEI was synthesized as illustrated in FIG. 1. Six-arm PEG was reacted with LPEI in PBS buffer. As the reaction progressed, NHS was separated from each arm of PEG with an amide bond formed between PEG and PEI (Scheme 1). In this step, the ester group of PEG which remained unreacted was hydrolyzed. Conjugation was analyzed through $^1$H-NMR spectra. Peaks were read at 3.69 ppm (FIG. 2a) and 2.71 ppm (FIG. 2b) for 6-arm PEG and LPEI, respectively. After reaction, two peaks were found at 3.70 and 3.01 ppm for the two products (FIGS. 2c and 2d), respectively. The integration ratios of the peak at 3.70 ppm to the peak at 3.01 ppm were 6:3 and 6:6 for the two different products, respectively, indicating that the product polymers were h-arm PEGs with three and six LPEI chains, respectively. They were termed MAPEG-LPEI$_3$ and MAPEG-LPEI$_6$, respectively.

Figure 3:
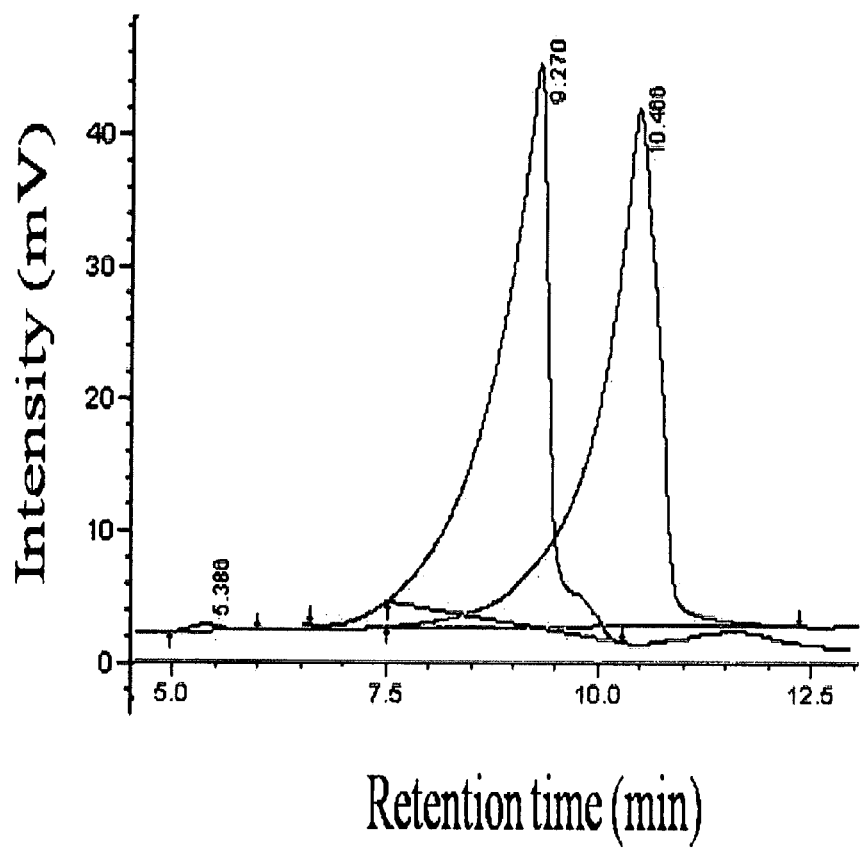
FIG. 3 is spectra of size extrusion chromatography for MAPEG-LPEI$_6$ and MAPEG-LPEI$_3$.

This was also confirmed in size exclusion chromatography spectra (FIG. 3). As seen in FIG. 3, MAPEG-LPEI$_6$ and MAPEG-LPEI$_3$ were eluted at 9.27 and 10.47 min, respectively, indicating that MAPEG-LPEI$_6$ is bigger than MAPEG-LPEI$_3$. Thanks to the PEG moiety, both MAPEG-LPEI$_3$ and MAPEG-LPEI$_6$ are water soluble.

2. Characterization of Polyplexes

Polyplexes were prepared by mixing each polymer solution at various N/P ratios with the pDNA solution. In order to detect the formation of polyplexes, gel retardation assay was performed on 1 wt % agarose gel (FIG. 4), with the use of free pDNA as a control.

Figure 4:
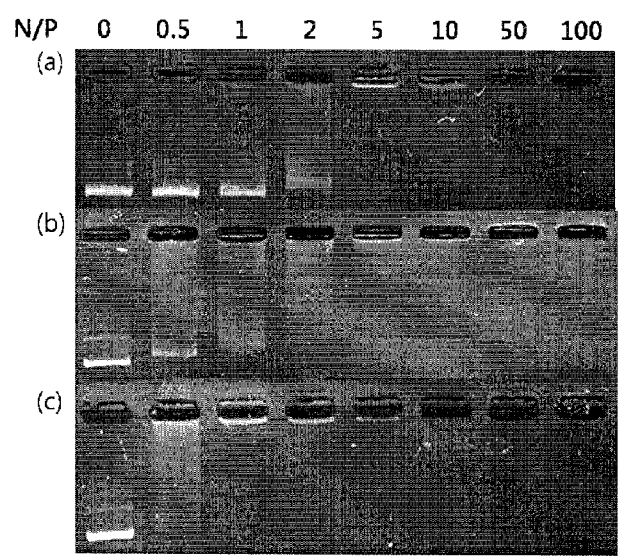
FIG. 4 shows results of gel retardation assay for polyplexes with N/P ratios of 5 (LPEI/pDNA) (a), 10 (MAPEG-LPEI$_3$) (b) and 2 (MAPEG-LPEI$_6$) (c) on 1 wt % agarose gel while a salt and free pDNA serve as controls.

The polyplexes were found to successfully retard DNA migration. With reference to FIG. 4, gel retardation assay results are shown for N/P ratio 5 (LPEI/pDNA), 10 (MAPEG-LPEI$_3$) and 2 (MAPEG-LPEI$_6$), together with other N/P ratios, indicating the formation of complete polyplexes, with the strongest attraction induced by MAPEG-LPEI$_6$. Differences in attraction account for structural differences between LPEI and MAPEG-LPEIs. LPEI is of a linear structure whereas MAPEG-LPEI$_3$ has an arm structure. MAPEG-LPEI$_6$ more readily interacts with pDNA. Due to the relative large size of the PEG moiety, MAPEG-LPEI$_3$, however, showed the lowest interaction with pDNA.

Figure 5:
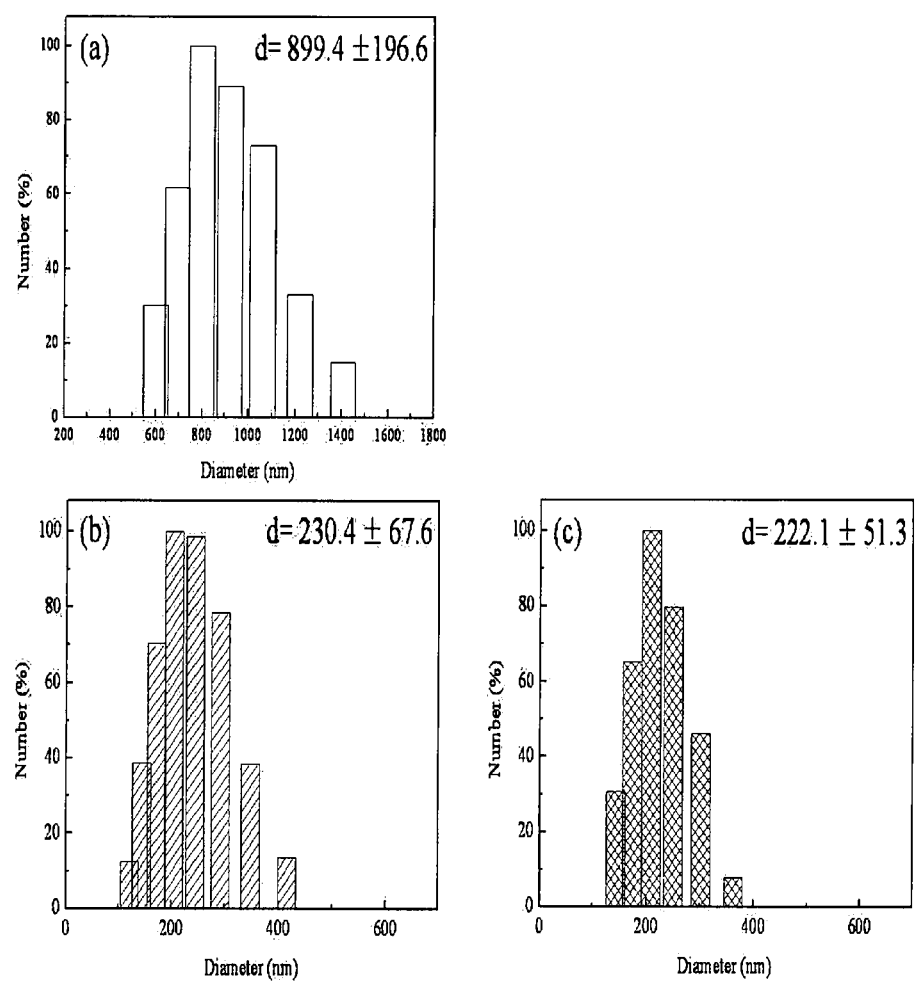
FIG. 5 is graphs of dynamic light scattering at an N/P ratio of 10 with LPEI (a), MAPEG-LPEI$_3$ (b) and MAPEG-LPEI$_6$ (c).

The polyplexes at N/P ratio 10 were analyzed for particle size using dynamic light scattering, the results of which are graphically depicted in FIG. 5. As seen in FIG. 5, MAPEG-LPEI$_6$ and MAPEG-LPEI$_3$ are observed to compress pDNA into small particles (about 200 nm) while LPEI forms far larger particles (about 900 nm) with pDNA. The large sizes of LPEI polyplexes are attributed to the fact that the linearity of PEI limits the foldability of the chain. The DLS (dynamic light scattering) data demonstrate that both MAPEG-LPEI$_6$ and MAPEG-LPEI$_3$ form particles small enough to act as gene carriers.

Figure 6:
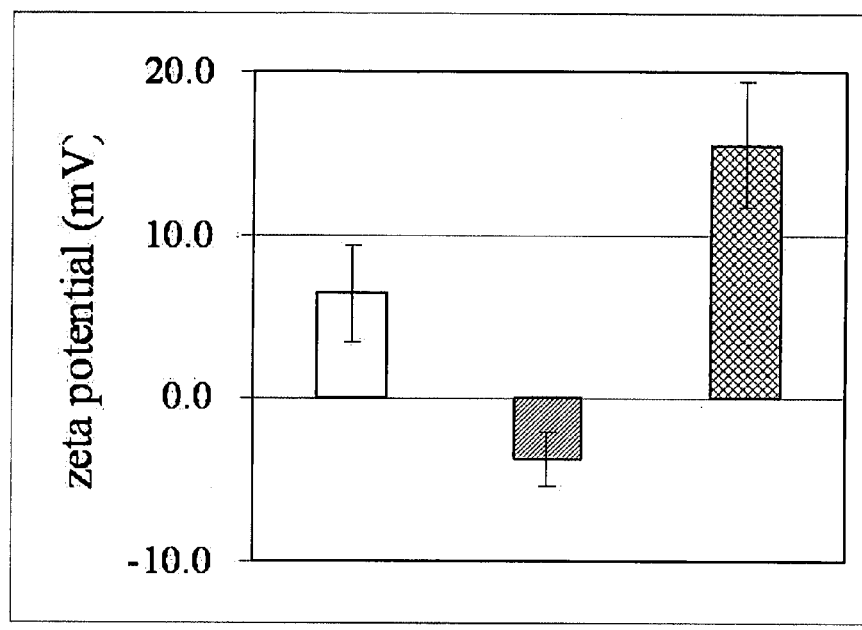
FIG. 6 is a graph of surface potentials of polyplexes at an N/P ratio of 10.

In addition, the polyplexes with N/P ratio 10 were determined for surface potential. As seen in FIG. 6, zeta potential data were measured to be +15.6 mV for the MAPEG-LPEI$_6$/pDNA polyplex, +6.5 mV for the LPEI/pDNA polyplex, 1.7 mV for the MAPEG-LPEI$_3$/pDNA polyplex, showing coincidence with the gel retardation assay data. In FIG. 4, positive charges were found in the MAPEG-LPEI$_6$ polyplex at N/P ratio 2 and in the polyplex at N/P ratio 10. Hence, the MAPEG-LPEI$_6$ polyplexes take the highest positive charges on the surface thereof whereas MAPEG-LPEI$_3$ takes negative charges due to the carboxyl group formed upon the hydrolysis of the non-reacted groups on PEG-SS. The LPEI polyplex was slightly positively charged on the surface thereof.

On the whole, smaller particles are better in transfection efficiency and higher surface potentials show higher cytotoxicity. Accordingly, MAPEG-LPEI$_6$ seems to be effective as a gene carrier.

3. In Vitro Assay

Figure 7:
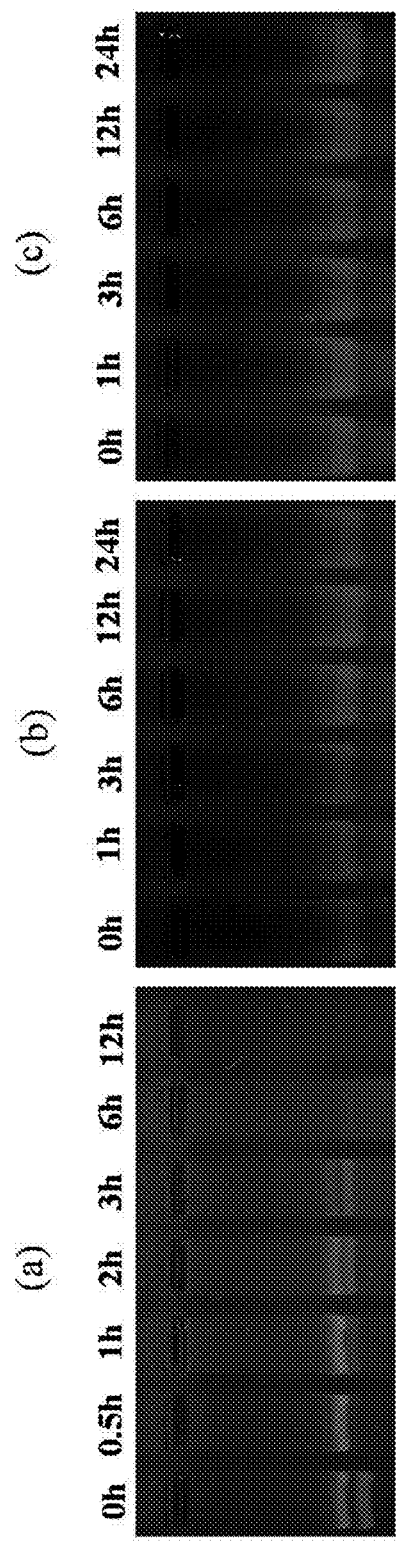
FIG. 7 shows the retention of DNA with time when pDNA (a), MAPEG-LPEI$_3$/pDNA polyplex (b) and MAPEG-LPEI$_6$/pDNA polyplex (c) were incubated with serum enzymes.

In order to determine the ability of the polymers to protect pDNA from serum enzymes, MAPEG-LPEI$_3$/pDNA polyplex, MAPEG-LPEI$_6$/pDNA polyplex, and free pDNA as a control were incubated at 37° C. while monitoring the damage of pDNA at regular intervals. As seen in FIG. 7, bands of free pDNA were observed to disappear within 6 hours after incubation.

In contrast, both the polyplexes MAPEG-LPEI$_3$/pDNA and MAPEG-LPEI$_6$/pDNA preserved pDNA for 24 hours as observed in DNA bands, indicating that MAPEG-LPEI protects pDNA from serum enzymes. That is, the polymer encompasses pDNA to prevent enzymes from contact with pDNA. As a result, MAPEG-LPEI can perfectly protect pDNA.

Figure 8:
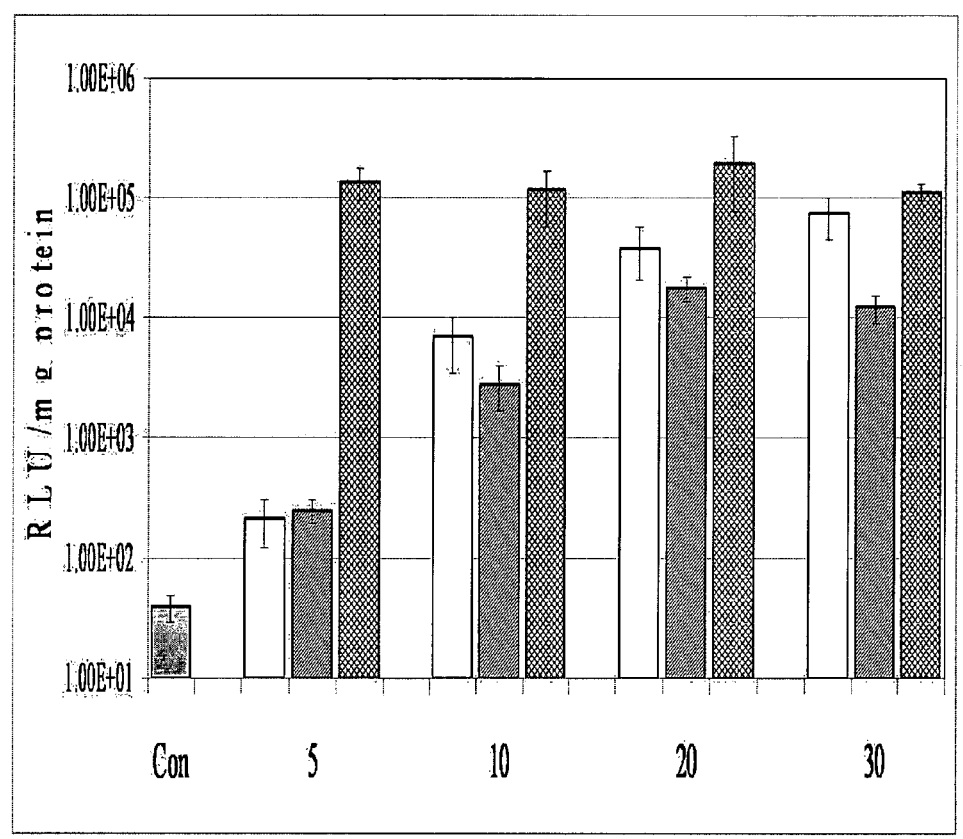
FIG. 8 is a graph showing transfection efficiencies of LPEI (left), MAPEG-LPEI$_3$ (middle) and MAPEG-LPEI$_6$ (right), with non-treatment used as a control.

Also, the gene carriers were assayed for transfection efficiency. For this, MAPEG-LPEI$_3$ or MAPEG-LPEI$_6$ complexed with pCMV-Luc expressing luciferase was transfected into HeLa cells at various w/w ratios of from 5 to 30. For comparison, the cells were transfected with the LPEI (25 K) polyplex, as well. Among the gene carrier, MAPEG-LPEI$_6$ was found to ensure the highest transfection efficiencies over the whole range, with a peak at a w/w ratio of 5, as seen in FIG. 8. The MAPEG-LPEI$_6$ was at least ten times higher in transfection efficiency over the whole range than was the MAPEG-LPEI$_3$. At a w/w ratio of 30, similar transfection efficiencies were detected between MAPEG-LPEI$_3$ and LPEI.

Figure 9:
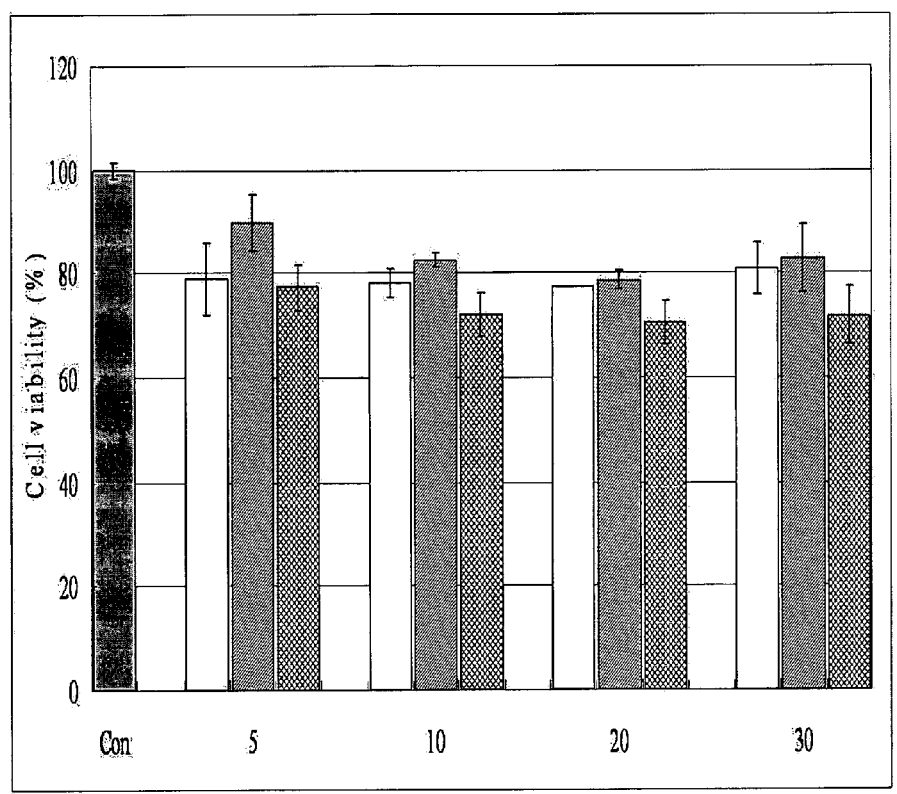
FIG. 9 is a graph showing cell viability of LPEI (left), MAPEG-LPEI$_3$ (middle) and MAPEG-LPEI$_6$ (right), with non-treatment used as a control.

Further, MAPEG-LPEI$_3$ and MAPEG-LPEI$_6$ were assayed for cytotoxicity using MTT assay. LPEIs were used for comparison. As shown in FIG. 9, the lowest cytotoxicity was detected from MAPEG-LPEI$_3$ polyplexes among the polyplexes while the MAPEG-LPEI$_6$ polyplex was similar in cytotoxicity to the LPEI polyplex. Both MAPEG-LPEI$_3$ and MAPEG-LPEI$_6$ ensured 70% higher cell viability than did LPEI.

MAPEG-LPEIs have characteristic structures in which the PEG moiety is located as a core with the PEI moiety exposed to the surface. In addition, PEI is of low molecular weight (2.5K) with low cytotoxicity. Thus, MAPEG-LPEI acts like LPEI (25K) in spite of a low portion of the PEI moiety. Accordingly, MAPEG-LPEIs can transfect at high efficiency into cells but with low cytotoxicity.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A compound of Chemical Formula 1

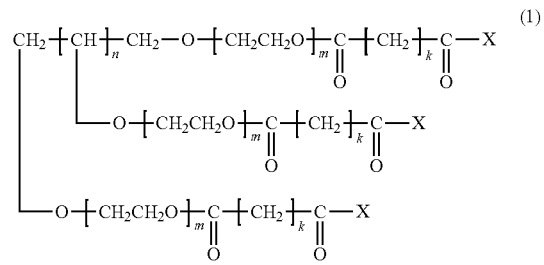

wherein,
n is an integer from 1 to 4,
m is different or the same integers representing repeat units,
k is an integer from 1 to 8, and
X is NH-A for 1 to (n+1) of the arms wherein A represents —CH$_2$CH$_2$—(NHCH$_2$CH$_2$)—NHCH$_2$CH$_2$NH$_2$, Z is an integer, and X is —OH for the remainder of the arms, or a salt or ester thereof.

2. The compound according to claim 1, wherein,
n is 4,
m is an integer representing a repeat unit for all arms, and
k is 2, or the salt or ester thereof.

3. The compound according to claim 1 or 2, wherein,
z is an integer from 10 to 500, and
m is an integer from 10 to 1000, or the salt or ester thereof.

4. A compound of Chemical Formula 4:

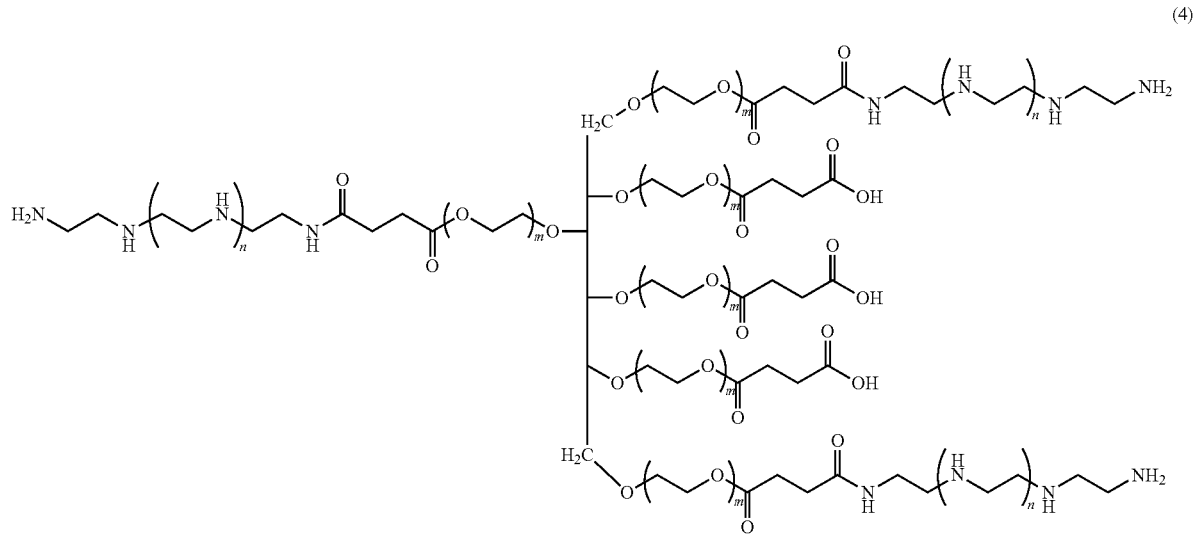

wherein m and n are independently integers representing repeat units.

5. A method of synthesizing a gene carrier, comprising reacting an arm-type polyethyleneglycol, of Chemical Formula 5:

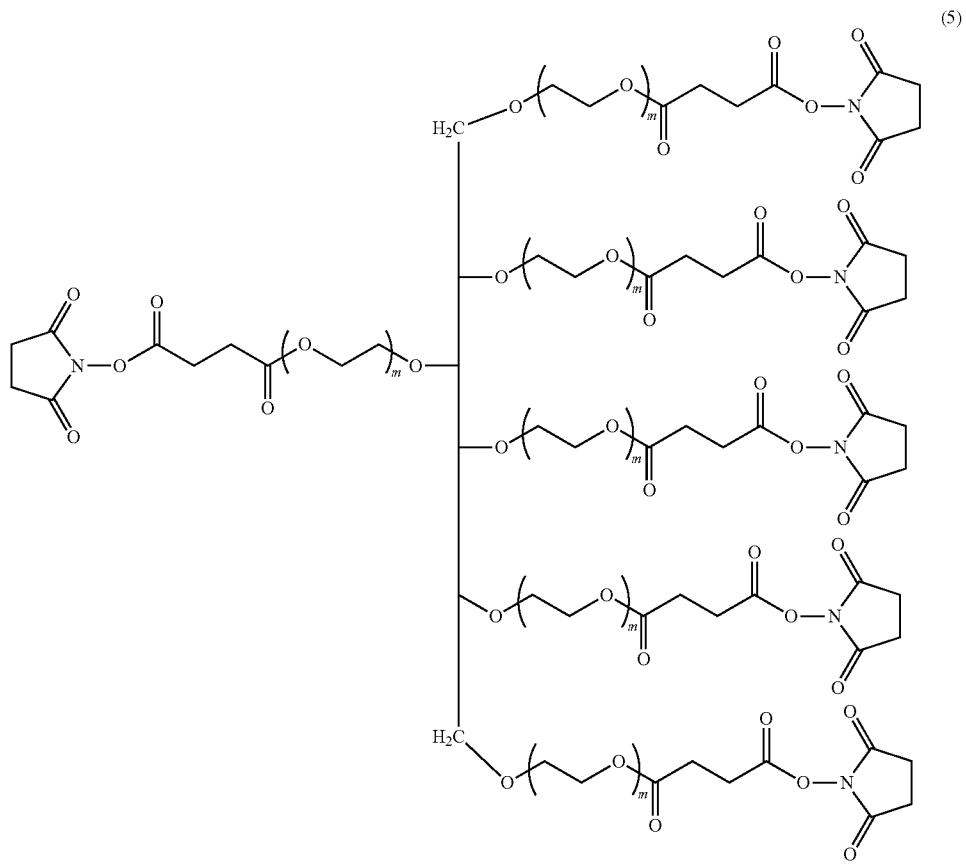

wherein m is integers which are representing repeat units, with a polyethyleneimine represented by Chemical Formula 6:

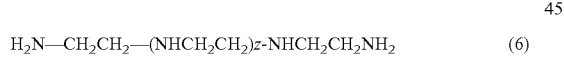

$H_2N-CH_2CH_2-(NHCH_2CH_2)_z-NHCH_2CH_2NH_2$ (6)

wherein z is an integer, and
wherein the polyethyleneglycol is hydrolyzed at the ester bond on at least one arm which remains unconjugated with the polyethyleneimine upon the reaction.

6. The method according to claim 5, wherein the polyethyleneglycol is conjugated on at least one arm with polyethyleneimine.

7. The method according to claim 5 or 6, wherein the polyethyleneglycol is conjugated on 3 arms with polyethyleneimine.

8. The method according to claim 5 or 6, wherein the reacting is carried out in a buffer containing an acid.

9. The method according to claim 5 or 6, wherein the arm-type polyethyleneglycol ranges in molecular weight from 5 to 20 K and the linear polyethyleneimine ranges in molecular weight from 1 to 10 K.

10. A polymer-gene complex, comprising:
a compound composed of arm-type polyethyleneglycol conjugated with linear polyethyleneimine, of Chemical Formula 1:

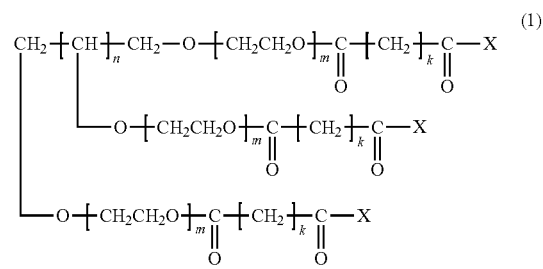

Wherein,
n is an integer from 1 to 4,
m is different or the same integers representing repeat units,
k is an integer from 1 to 8, and
X is NH-A for 1 to (n+1) of the arms wherein A represents —$CH_2CH_2$—$(NHCH_2CH_2)$—$NHCH_2CH_2NH_2$, Z is an integer, and X is —OH for the remainder of the arms, or a salt or ester thereof.

11. The polymer-gene complex according to claim 10, wherein the gene is DNA and/or RNA.

12. The polymer-gene complex according to claim 10 or 11, wherein the complex is 300 nm or less in size.

13. The polymer-gene complex according to claim 10 or 11, wherein the complex is 200 nm or less in size.

14. The polymer-gene complex according to claim 10 or 11, wherein the polyethyleneimine moiety has a molecular weight of 2.5 K.

15. The polymer-gene complex according to claim 10 or 11, wherein the polyethyleneglycol moiety has a molecular weight of from 5 to 20 K.

16. The polymer-gene complex according to claim 10, being water-soluble.

17. A method for transferring a gene, comprising:
    reacting a three- to six-arm type polyethyleneglycol with polyethyleneimine to afford a conjugated compound; and
    associating the conjugated compound with a gene, wherein the polyethyleneglycol has an ester group on at least one arm.

18. The method according to claim 17, wherein the polyethyleneglycol is conjugated at least one arm via an amide bond with the polyethyleneimine.

19. The method according to claim 18, wherein the polyethyleneglycol is of a six-arm type structure.

20. The method according to 18, wherein the polyethyleneglycol has an N-hydroxysuccinimide ester group at an end of at least one arm.

* * * * *

UNITED STATES PATENT AND TRADEMARK OFFICE
CERTIFICATE OF CORRECTION

PATENT NO. : 9,115,057 B2  
APPLICATION NO. : 13/122667  
DATED : August 25, 2015  
INVENTOR(S) : Kim and Namgung Page 1 of 1

It is certified that error appears in the above-identified patent and that said Letters Patent is hereby corrected as shown below:

In The Claims

Claim 1, Column 18, line 27 reads:

-- -$CH_2CH_2$-($NHCH_2CH_2$)-$NHCH_2CH_2NH_2$, Z is an --

Claim 1, Column 18, line 27 should read:

-- -$CH_2CH_2$-($NHCH_2CH_2$)$_Z$-$NHCH_2CH_2NH_2$, Z is an --

Claim 10, Column 20, line 61 reads:

-- -$CH_2CH_2$-($NHCH_2CH_2$)-$NHCH_2CH_2NH_2$, Z is an --

Claim 10, Column 20, line 61 should read:

-- -$CH_2CH_2$-($NHCH_2CH_2$)$_Z$-$NHCH_2CH_2NH_2$, Z is an --

Signed and Sealed this  
Twenty-ninth Day of December, 2015

Michelle K. Lee  
*Director of the United States Patent and Trademark Office*